(12) United States Patent
Den Brinker et al.

(10) Patent No.: US 9,907,474 B2
(45) Date of Patent: Mar. 6, 2018

(54) SIGNAL SELECTION FOR OBTAINING A REMOTE PHOTOPLETHYSMOGRAPHIC WAVEFORM

(71) Applicant: KONINKLIJKE PHILIPS N.V., Eindhoven (NL)

(72) Inventors: Albertus Cornelis Den Brinker, Eindhoven (NL); Murtaza Bulut, Eindhoven (NL); Vincent Jeanne, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/024,668

(22) PCT Filed: Sep. 25, 2014

(86) PCT No.: PCT/EP2014/070444
§ 371 (c)(1),
(2) Date: Mar. 24, 2016

(87) PCT Pub. No.: WO2015/049150
PCT Pub. Date: Apr. 9, 2015

(65) Prior Publication Data
US 2016/0220128 A1    Aug. 4, 2016

(30) Foreign Application Priority Data

Oct. 1, 2013  (EP) ..................................... 13186810

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0006* (2013.01); *A61B 5/0008* (2013.01); *A61B 5/02416* (2013.01); *A61B 5/08* (2013.01); *A61B 5/0816* (2013.01); *A61B 5/14551* (2013.01); *A61B 5/14552* (2013.01); *A61B 5/7203* (2013.01)

(58) Field of Classification Search
CPC . A61B 5/02055; A61B 5/0006; A61B 5/0008; A61B 5/08; A61B 5/14552
See application file for complete search history.

(56) References Cited

U.S. PATENT DOCUMENTS

| | | | |
|---|---|---|---|
| 8,649,562 B2 * | 2/2014 | De Haan | G06T 7/20 382/103 |
| 2009/0105556 A1 | 4/2009 | Fricke | |

(Continued)

FOREIGN PATENT DOCUMENTS

| | | |
|---|---|---|
| WO | 2011/042858 | 4/2011 |
| WO | 2013/027027 | 2/2013 |

(Continued)

OTHER PUBLICATIONS

Verkruysse et al., "Remote plethysmographic imaging using ambient light", Optics Express, 16(26), Dec. 22, 2008, pp. 21434-21445.
(Continued)

*Primary Examiner* — Manuel L Barbee

(57) ABSTRACT

The present invention relates to a device (22) for processing input signals (34a, 34b) related to a vital sign of a subject (10), comprising an interface (24) for receiving a non-invasively detected input signal (34a, 34b), a feature extraction module (26) for extracting at least one feature of the input signal (34a, 34b), said at least one feature including an instantaneous frequency representation (40a, 40b) of the input signal (34a, 34b) and/or an instantaneous amplitude representation (42a, 42b) of the input signal (34a, 34b), a processing module (28) for determining a signal information content parameter (52) for the input signal (34a, 34b) based on the at least one extracted feature, said signal information content parameter (52) being indicative of information on a vital sign of the subject (10) included in the input signal (34a, 34b) and a combination module (30) for combining a plurality of input signals based on the signal information content parameters (52) of the plurality of input signals into a combined output signal characterizing the vital sign of the subject (10). The present invention further relates to a
(Continued)

corresponding method and to a monitoring system (12) for remotely monitoring a vital sign of a subject (10).

20 Claims, 5 Drawing Sheets

(51) Int. Cl.
*A61B 5/08* (2006.01)
*A61B 5/1455* (2006.01)
*A61B 5/024* (2006.01)

(56) References Cited

U.S. PATENT DOCUMENTS

2012/0190947 A1* 7/2012 Chon ............... A61B 5/02405
600/323
2013/0041277 A1 2/2013 Hsiao

FOREIGN PATENT DOCUMENTS

WO 2013/027141 2/2013
WO 2013/038326 2/2013

OTHER PUBLICATIONS

Barnes, "The Calculation of Instantaneous Frequency and Instantaneous Bandwidth", in Geophysics, vol. 57, No. 11, Nov. 1992, pp. 1520-1524.
Picinbono, "On instantaneous amplitude and phase of signals", in IEEE Transactions on Signal Processing, vol. 45, No. 3, Mar. 1997.
Wu, "PPGI: New Development in Noninvasive and Contactless Diagnosis of Dermal Perfusion Using Near InfraRed Light", J. of the GCPD e.V., vol. 7, No. 1, Oct. 2003.
Allen, "Photoplethysmography and its application in clinical physiological measurement", Physiol. Meas. 28 (2007) R1-R39.

* cited by examiner

SIGNAL SELECTION FOR OBTAINING A REMOTE PHOTOPLETHYSMOGRAPHIC WAVEFORM

CROSS REFERENCE TO RELATED APPLICATIONS

This application is the U.S. National Phase application under 35 U.S.C. § 371 of International Application No. PCT/EP2014/070444, filed Sep. 25, 2014, published as WO 2015/049150 on Apr. 9, 2015, which claims the benefit of European Patent Application Number 13186810.1 filed Oct. 1, 2013. These applications are hereby incorporated by reference herein.

FIELD OF THE INVENTION

The present invention relates to a device and method for processing input signals. The present invention further relates to a monitoring system for remotely monitoring a vital sign of a subject. In particular, the present invention relates to evaluating remotely detected optical signals in order to obtain a meaningful remote photoplethysmographic (RPPG) waveform.

BACKGROUND OF THE INVENTION

Vital signs of a person, for example the heart rate (HR), the respiration rate (RR) or the blood oxygen saturation, serve as indicators of the current state of a person and as powerful predictors of serious medical events. For this reason, vital signs are extensively monitored in inpatient and outpatient care settings, at home or in further health, leisure and fitness settings.

One way of measuring vital signs is plethysmography. Plethysmography generally refers to the measurement of volume changes of an organ or a body part and in particular to the detection of volume changes due to a cardio-vascular pulse wave traveling through the body of a subject with every heart beat.

Photoplethysmography (PPG) is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Besides information about the heart rate, a PPG waveform can comprise information attributable to further physiological phenomena such as the respiration. By evaluating the transmissivity and/or reflectivity at different wavelengths (typically red and infrared), the blood oxygen saturation can be determined.

Conventional pulse oximeters for measuring the heart rate and the (arterial) blood oxygen saturation of a subject are attached to the skin of the subject, for instance to a finger tip, earlobe or forehead. Therefore, they are referred to as 'contact' PPG devices. A typical pulse oximeter comprises a red LED and an infrared LED as light sources and one photodiode for detecting light that has been transmitted through patient tissue. Commercially available pulse oximeters quickly switch between measurements at a red and an infrared wavelength and thereby measure the transmissivity of the same area or volume of tissue at two different wavelengths. This is referred to as time-division-multiplexing. The transmissivity over time at each wavelength gives the PPG waveforms for red and infrared wavelengths. Although contact PPG is regarded as a basically non-invasive technique, contact PPG measurement is often experienced as being unpleasant, since the pulse oximeter is directly attached to the subject and any cables limit the freedom to move.

Recently, non-contact, remote PPG (RPPG) devices for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications.

Verkruysse et al., "Remote plethysmographic imaging using ambient light", Optics Express, 16(26), 22 Dec. 2008, pp. 21434-21445 demonstrate that photoplethysmographic signals can be measured remotely using ambient light and a conventional consumer level video camera.

One of the main advantages of camera-based vital signs monitoring over on-body sensors is the high ease-of-use: there is no need to attach a sensor, just aiming the camera at the skin/chest of the subject is sufficient. Another advantage of camera-based vital signs monitoring over on-body sensors is the potential for achieving motion robustness: cameras have a significant spatial resolution while contact sensors mostly consist of a single element detector.

One of the key challenges for this technology is to be able to provide robust measurement under motion/light distortions. Several methods have been developed to enable robust camera-based vital signs measurement. For such measurements, usually a plurality of signals is captured based on image processing of captured image or image sequence. The plurality of signals may originate from different pixels of a sensor or also from different color channels of one pixel or of the same spatial position. Then, a photoplethysmographic waveform is formed based on a plurality of the signals. This waveform is the basis for further analysis, such as the determination of vital signs of a subject.

In WO 2013/027027 A2 there is disclosed a method for remotely monitoring vital signs by detecting a PPG signal in an image of a subject taken by a video camera such as a webcam. The PPG signal is identified by auto-regressive analysis of ambient light reflected from a region of interest on the subject's skin. Frequency components of the ambient light and aliasing artifacts resulting from the frame rate of the video camera are cancelled by auto-regressive analysis of ambient light reflected from a region of interest not on the subject's skin, e.g. in the background. This reveals the spectral content of the ambient light allowing identification of the subject's PPG signal.

In US 2013/041277 A1 a method for extracting the feature of an abdominal breathing and a system using the same are disclosed. The method is, capable of extracting the feature of an abdominal breathing, without the requirement of a standard model of an abdominal breathing and the execution of a learning process being executed prior to the method for extracting the feature of an abdominal breathing. By means of computing a plurality of intrinsic mode functions corresponding to the abdominal breathing signal received, an Euler angle function and an instantaneous frequency function of each of the plurality of intrinsic mode functions, and comparing the plurality of instantaneous frequency function with a pre-determined zero-point threshold region, the method for extracting the feature of an abdominal breathing defines one of the plurality of instantaneous frequency function as an abdominal breathing feature function, which contains the feature of the abdominal breathing. In this way, the feature of an abdominal breathing is extracted.

There exist various other approaches that rely on the spectral energy when it comes to the point of selecting the right set of signals to form a remote photoplethysmographic waveform i.e. a subject's PPG signal. This, however, implies that any distortion exhibiting strong frequency component inside the heart-rate bandwidth (0.5-3.5 Hz) may also be perceived as good candidate for the remote photoplethysmographic waveform generation. This often leads to unreliable waveforms.

SUMMARY OF THE INVENTION

It is an object of the present invention to provide a device and a method for processing non-invasively detected signals related to a vital sign of a subject that improve the acquisition of reliable vital signs of the subject.

In a first aspect of the present invention, there is presented a device for processing input signals related to a vital sign of a subject, comprising an interface for receiving a non-invasively detected input signal, a feature extraction module for extracting at least one feature of the input signal, said at least one feature including an instantaneous frequency representation of the input signal and/or an instantaneous amplitude representation of the input signal, a processing module for determining a signal information content parameter for the input signal based on the at least one extracted feature, said signal information content parameter being indicative of information on a vital sign of the subject included in the input signal, and a combination module for combining a plurality of input signals based on the signal information content parameters of the plurality of input signals into a combined output signal characterizing the vital sign of the subject.

In a further aspect of the present invention a corresponding method for processing input signals related to a vital sign of a subject is presented.

In yet another aspect of the present invention, there is presented a monitoring system for remotely monitoring a vital sign of a subject comprising a sensor for converting light reflected from a region of interest into a data stream and for extracting at least one input signal from said data stream, a device as described above and an evaluation unit for determining vital sign information of the subject based on the at least one input signal.

In yet further aspects of the present invention, there is provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system and computer program have similar and/or identical preferred embodiments as the claimed device and as defined in the dependent claims.

The present invention allows evaluating non-invasively detected signals from which vital signs of a subject, e.g. a person such as a patient or a sportsperson, can be obtained. As used herein, an input signal or a non-invasively detected input signal refers to a development of a measure (e.g. a value measured by a sensor) over time or to a sample of said development of said measure, i.e. a section of said development. In particular, an input signal may refer to a digital representation of an analog signal obtained from a physical phenomenon, such as fluctuating light intensity, measured by means of a non-invasive method (e.g. by means of a camera or a camera pixel).

According to the present invention, features are extracted from the input signal, these features particularly including an instantaneous frequency representation and/or an instantaneous amplitude representation of the input signal. These features are analyzed in a processing module and a signal information content parameter is determined, which is indicative of information on a vital sign of the subject included in the input signal.

The instantaneous frequency representation of an input signal corresponds to the derivative of the instantaneous phase of the signal. Details and multiple approaches on how to calculate the instantaneous frequency of a signal can be found in Barnes, "The Calculation of Instantaneous Frequency and Instantaneous Bandwidth", in Geophysics, Vol. 57, No. 11, Nov. 1992, pages 1520-1524, wherein multiple ways for deriving an instantaneous frequency representation of a signal are outlined.

Alternatively or additionally to the instantaneous frequency representation of the input signal, also the instantaneous amplitude representation can be used. Said instantaneous amplitude representation as used herein corresponds to the signal envelope of the input signal. Further information on the instantaneous amplitude representation of a signal can also be found in Picinbono, "On instantaneous amplitude and phase of signals", in IEEE Transactions on Signal Processing, Vol. 45, No. 3, Mar. 1997.

If both the instantaneous frequency representation and the instantaneous amplitude representation of the input signal are used the reliability of determining whether the input signal includes information on a vital sign of a subject may be increased. There may be determined one signal information content parameter for the instantaneous amplitude representation and another one for the instantaneous frequency representation, i.e. one signal information content parameter for each feature. There may, however, also be determined multiple signal information content parameters for each of the features or also combined signal information content parameters based on both features (or multiple features in other embodiments).

A signal information content parameter as used herein can basically refer to any kind of parameter being determined based on an input signal. One the one hand, a signal information content parameter may refer to a value that is derived from the input signal by means of a mathematical operation (e.g. a standard deviation or the like). On the other hand, a signal information content parameter may also refer to a value that is determined by additionally including further information such as threshold or reference values (e.g. whether a standard deviation is above a threshold). In particular, a signal information content parameter may refer to a measure of the information content of a signal with regard to a vital sign of a patient (i.e. if the signal carries information on a vital sign). A signal information content parameter may thus refer to a quality measure of the considered signal indicating whether (and to what extent) the signal carries information on a vital sign or whether (and to what extent) the signal is distorted. Examples therefor may include quality measures on a predefined numeric scale or binary values. A signal information content parameter may also include multiple separate values or parameters, e.g. a first binary value of whether or not the signal is to be considered at all in the further processing and a second numeric value indicating which specific vital sign the input signal seems to be a good indication for.

The interface for receiving the input signal may refer to a data interface such as a wired or wireless connection over which information, i.e. the input signal, comes into the device. The interface may also refer to a complete sensor system for obtaining an input signal, e.g. an input signal that is derived from electromagnetic radiation reflected from a region of interest including a skin area of a subject such as a photodiode, camera or other sensor.

The term "vital sign" as used in the context of the present invention refers to a physiological parameter of a subject (i.e. a living being) and derivative parameters. In particular, the term "vital sign" comprises heart rate (HR) (sometimes also called "pulse rate"), heart rate variability (pulse rate variability), pulse utility strength, perfusion, perfusion variability, PPG pulse utility, Traube-Hering-Mayer waves, respiratory rate (RR), body skin temperature, blood pressure, pulse transit time (PTT), concentration of a substance in blood and/or tissue, such as (arterial) blood oxygen saturation or glucose level. The term "information on a vital sign" as used in the context of the present invention comprises the one or more measured vital signs as defined above. Furthermore, it comprises data referring to a physiological parameter, corresponding waveform traces or data referring to a physiological parameter of a time that can serve for a subsequent analysis.

The proposed device allows determining a signal information content parameter, which indicates whether said signal includes information on a vital sign of the subject or whether it is disturbed by, e.g., noise or motion. Advantages of the present invention particularly include a higher reliability and accuracy of the selection in comparison to previous approaches. Previous approaches mainly rely on the spectral energy for selecting a signal. In comparison thereto, the present invention makes use of the instantaneous frequency representation and/or the instantaneous amplitude representation of the signal. It thereby becomes possible to provide an improved selection of input signals. For instance, it becomes possible to filter distortions with frequency components inside the heart-rate bandwidth (approximately 0.5-3.5 Hz) that may be perceived as good candidates for the remote photoplethysmographic waveform generation if only frequency filtering were applied. Other bandwidths can be used depending on the targeted vital sign.

The device of the present invention further comprises a combination module for combining a plurality of input signals based on the signal information content parameters of the plurality of input signals into a combined output signal characterizing the vital sign of the subject. Said combination module receives a plurality of input signals and corresponding signal information content parameters. Each of the signal information content parameters indicates whether its corresponding input signal includes meaningful information on a vital sign of the subject. This information is considered when the input signals are combined. The combined output signal thereby particularly refers to a photoplethysmographic waveform. Based on such a photoplethysmographic waveform it may be possible (in a further step) to extract a vital sign, e.g. the heart rate of the subject. Herein, combining may, e.g., refer to determining the average (weighted or arithmetic) of subset of the input signals that are determined to include information on the vital sign. The combination module provides an output signal that may be further processed and allows including only those input signals into the output signal that are assumed to represent the vital sign. Bad input signals, i.e. input signals resulting from distortions, are usually not considered which is not a problem e.g. for remote PPG where a large number of input signals acquired by a camera (generally one input signal per pixel or pixel group) are available. By considering the instantaneous frequency representation and/or the instantaneous amplitude representation, the physiological properties of the remote photoplethysmographic waveform may be optimally explored for selecting the input signals to include in the output signal.

In another embodiment of the present invention, the feature extraction module is configured to determine an analytic representation of the input signal by applying a Hilbert transform to the input signal and to determine the absolute value of the analytic representation of the input signal for extracting the instantaneous amplitude representation of the input signal. The analytic representation of a signal refers to a complex-valued time signal of which the imaginary part corresponds to the Hilbert transform of the real part. One approach to determine the instantaneous amplitude (sometimes also referred to as signal envelope or amplitude envelope) of a signal includes calculating said analytic signal representation. Determining the absolute value therefrom gives the instantaneous amplitude of the signal.

In another embodiment, the at least one extracted feature further includes a spectral representation of the input signal. Such a spectral representation refers to a representation of the different frequencies comprised in the input signal. Usually, a spectral representation (or frequency spectrum) includes an intensity value for each frequency component indicating the intensity of this frequency component in the input signal. A spectral representation may particularly be determined based on a time sample of an input signal or a segment of an input signal. A useful way of determining a spectral representation of the input signal includes transforming the input signal by means of a Fourier transform.

According to a preferable embodiment, the feature extraction module is configured to determine an analytic representation of the input signal by applying a Hilbert transform to the input signal, to extract from the analytic representation of the input signal an instantaneous phase representation of the input signal and to determine the derivative of the instantaneous phase representation of the input signal or to determine the mean and/or variance (or standard deviation) of the distances between consecutive zero crossings of the input signal as parameters indicative of the instantaneous frequency representation of the input signal. One efficient way to compute the instantaneous frequency representation of a signal also includes determining the analytic signal representation by making use of the Hilbert transform as outlined above. From this analytic representation of the signal the instantaneous phase representation is directly derivable. The derivative of the instantaneous phase representation (or, more precisely, the time derivative of the unwrapped instantaneous phase) corresponds to the instantaneous frequency.

In another embodiment, the processing module is configured to determine a dominant frequency component of the input signal by calculating an average of the instantaneous frequency representation of the input signal. A preferable signal information content parameter is the dominant frequency. One possibility to calculate said dominant frequency component is by means of calculating the average of the instantaneous frequency representation. This dominant frequency component may then be compared to expected dominant frequency values for the desired vital sign of a subject. For instance, the heart rate or the breathing rate of a subject will have a distinct dominant frequency component within more or less predefined limits. This may be used to define a range criterion.

In another embodiment of the device, the processing module is configured to determine a standard deviation of the instantaneous frequency representation of the input signal and/or to determine a standard deviation of the instantaneous amplitude representation of the input signal. According to this embodiment, it is analyzed how strong the variations of the extracted instantaneous frequency and/or amplitude representation of the input signal are. Determining the standard deviation thereby gives a measure for fluctuations, i.e. variations. This measure can then be compared to knowledge about expected vital signs. For instance, distortions or distorted signals resulting from distortions in the form of single pulses (e.g. being caused by light flickering of the ambient light) may have an effect on the standard deviation of the instantaneous frequency or amplitude representation of the input signal. Thus, analyzing the standard deviations of the two features allows obtaining additional information (i.e. a signal information content parameter) in order to determine whether the input signal is indicative of a vital sign or not. If, e.g., the heart rate is considered, the standard deviation of both the instantaneous frequency and the instantaneous amplitude may usually be within certain limits. Alternatively to using the standard deviation, other parameters being indicative of the fluctuation of a signal may be used. Also, there may be used a linear or non-linear function of the standard deviation to be compared to a frequency variation threshold.

In another embodiment, the processing module is further configured to compare the standard deviation of the instantaneous frequency representation of the input signal with a frequency variation threshold and/or to compare the standard deviation of the instantaneous amplitude representation of the input signal with an amplitude variation threshold. One possible approach of making use of the determined standard deviations is by comparing them to threshold values and determining whether they are below or above a certain threshold. This allows efficiently selecting input signals based on their extracted instantaneous frequency and/or amplitude representation. Both the frequency variation threshold and/or the amplitude variation threshold may thereby either be predefined or updated during the operation of the device. A predefined threshold may, e.g., be determined from an experimental evaluation of external conditions in a usual application scenario, such as a hospital room (i.e. analyze the usual distortions). An adapted threshold may, e.g., be based on a moving average of the currently determined standard deviations. Then, outliers, i.e. values with unusual high value, may be rejected based on the adapted threshold.

In another embodiment, the processing module is configured to determine a dominant frequency component of the input signal by determining the frequency with the highest spectral intensity in a spectral representation of the input signal or by calculating an average of the instantaneous frequency representation of the input signal, and to determine whether the dominant frequency component of the input signal is within a frequency range. The dominant frequency component herein usually refers to the peak in the spectral representation of a signal. If this dominant component is out of this frequency range, the probability that the input signal does not include information on a vital sign of the patient may be higher if this vital sign is usually represented by a certain frequency. For example, a heart rate is usually in a frequency range of 0.5 Hz to 3.5 Hz. Thus, if the dominant frequency component of an input signal is not in this range, it is likely that the input signal at least not only includes information on the heart rate of the patient, but also other information, e.g. distortions resulting from flickering light or other distortion sources. The frequency range may herein refer to a predefined range or also to an adaptively updated range. A predefined range may be determined based on the expected frequencies for the vital sign to be determined. A predefined frequency range may also be experimentally determined. An adapted frequency range may include a range that is continuously updated during the operation of the system. One example for an adaptive frequency range may include a moving average of a continuously determined dominant frequency to which a certain percentage is added.

In yet another embodiment, the processing module is configured to determine a binary signal information content parameter for the input signal based on a conjunction of at least two threshold or range criteria applied to the signal information content parameter, said binary signal information content parameter indicating whether the input signal includes information on a vital sign of the subject. The information content parameter can thus be represented by or include a binary value (binary signal information content parameter). A conjunction represents a combination of several criteria that all have to be fulfilled. These criteria may particularly be threshold or range criteria. A threshold criterion may be represented by a comparison of the information content parameter to threshold value. A range criterion may be represented by determining whether the parameter is within a certain range. For example, the standard deviation of an instantaneous frequency representation of the input signal has to be below a certain threshold and the dominant frequency component has to be within a certain range. Again, the threshold or range criteria may be predefined or adaptively calculated. If the different signal information content parameters fulfill all threshold or range criteria (conjunction), then the binary signal information content parameter is set to one and indicates that the input signal is considered to be valid, i.e. to include meaningful information on a vital sign of the subject. Herein, a "valid" signal particularly refers to an input signal that can be used in the further signal processing and/or in the generation of a photoplethysmographic waveform.

According to another embodiment, the input signal is derived from electromagnetic radiation reflected from a region of interest including a skin area of the subject and the vital sign of the subject corresponds to the heart rate, respiration rate or blood oxygen saturation of a living subject. One important application area of the present invention is in the recognition of the heart rate or another vital sign of a person, i.e. a living subject such as a patient or a sportsperson, that is monitored, e.g., in a hospital or in a remote, telemedicine system. The main advantage is that the therefor required sensor can be a contactless sensor. For instance, an input signal from which vital signs of a subject can be derived may be obtained by means of photoplethysmography (PPG) or photoplethysmography (RPPG). RPPG may be carried out based on reflections of electromagnetic radiation from the skin of the subject. There are usually detected a plurality of signals that may, e.g., represent a time discrete or time continuous development of the light intensity registered by a single pixel or for a specific color. A subset of the detected signals may provide higher information content than others. For example, a part of the obtained image may be disturbed from light distortion or movements of the patient. The present invention may then provide an improved approach for evaluating the signals (input signals) and determining which of the signals can be considered good candidates for obtaining a meaningful remote photoplethysmographic waveform. Based on this waveform, it may then be possible to determine a vital sign of a patient, e.g. the heart rate, the blood oxygen saturation or the respiration rate, with higher reliability and accuracy. However, the present invention can also be used in other application areas.

According to yet another embodiment, the combination module is configured to determine an average of the plurality of input signals, said average being calculated based on attributing equal weights to the plurality of input signals or based on attributing individual weights to the plurality of input signals, in particular individual weights being calculated based on the signal information content parameters of the plurality of input signals. In particular, it is possible to attribute individual weights to the different input signals when determining the output signal, i.e. the photoplethysmographic waveform that then forms the basis for further evaluation (e.g. the determination or the monitoring of a vital sign). These individual weights may be calculated based on the signal information content parameters. If, e.g., one signal information content parameter represents a standard deviation, one way to determine an individual weight for the respective input signal (when calculating the output signal based on averaging multiple input signals) is to use the reciprocal value of the standard deviation. Thus, an input signal that strongly fluctuates is attributed a lower weight than an input signal with a more constant frequency. Other possibilities include particularly using a binary weight, i.e. including only a subset of the signals when calculating the average and attributing a zero weight to the others. The individual weights may also be calculated based on linear or nonlinear functions of one or more of the signal information content parameters.

Preferably, the combination module is configured to determine whether to use or discard an input signal for the combination of input signals based on the respective signal information content parameters and to combine only non-discarded input signals. Thus, as briefly mentioned above, from a large number of available input signals, many of them may be discarded if the signal information content parameter indicates that they may be disturbed or distorted. In a preferred embodiment, only the "very good" input signals for which the signal information content parameter clearly indicates that they are not disturbed or distorted will be used in the combination and, finally, contribute to the extraction of the desired vital sign.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
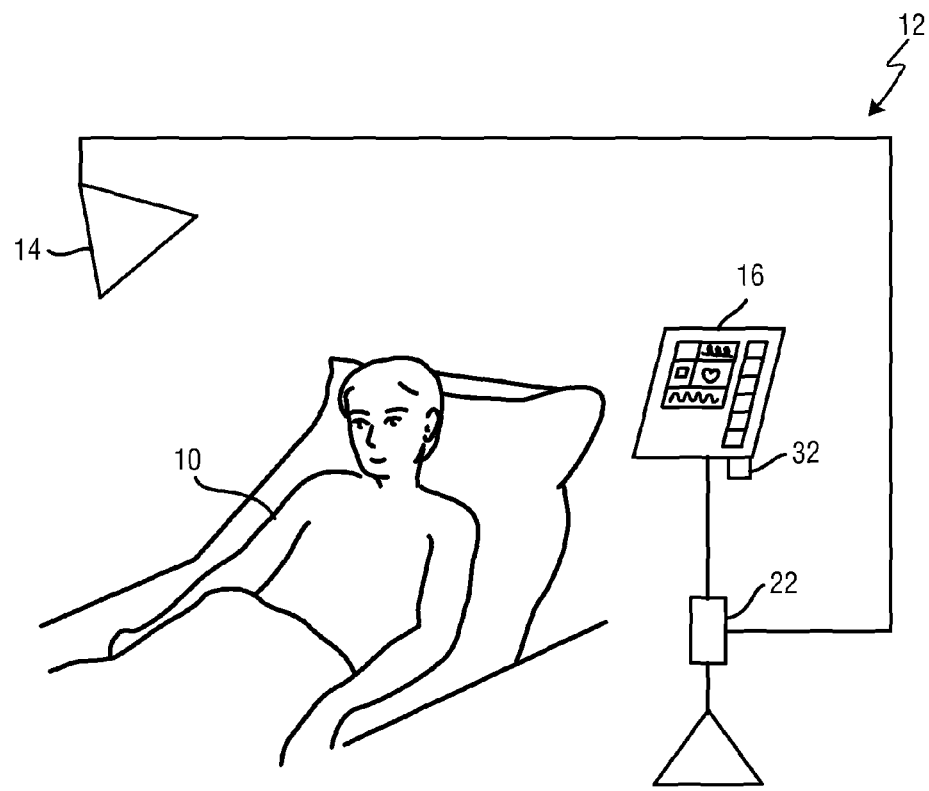
FIG. 1 shows a schematic illustration of a monitoring system according to an embodiment of the present invention.

FIG. 1 illustrates a patient 10 being hospitalized in a hospital bed. In such a hospitalization scenario the vital signs of the patient 10 need to be monitored. Conventional monitoring systems thereby usually rely on attachable sensors, i.e. body mounted sensors. In order to increase patient comfort, remote monitoring systems can be used, which can reduce the required cabling. In FIG. 1 there is illustrated a monitoring system 12 for remotely monitoring a vital sign of a patient 10 according to an aspect of the present invention. The illustrated system 12 thereby makes use of the remote photoplethysmographic measurement principle. Thereby, a camera 14 is used to capture an image, i.e. a video sequence of the patient 10. This camera can comprise a CCD or CMOS sensor for converting incident light and the intensity variations thereof into an electronic signal. The camera 14 particularly non-invasively captures light reflected from a skin portion of the patient 10. A skin portion may thereby particularly refer to the forehead or the chest of the patient. A light source, e.g. an infrared or visible light source, may be used to illuminate the patient or a region of interest including a skin portion of the patient. It may also be possible that the patient 10 is illuminated with light of a certain limited spectrum or that two specific spectra (i.e. colors) are captured separately in order to analyze differences resulting therefrom. Based on the captured images, information on a vital sign of the patient 10 can be determined. In particular, vital signs such as the heart rate, the breathing rate or the blood oxygenation of the patient 10 can be determined. The determined information is usually displayed on an operator interface 16 for presenting the determined vital sign. Such an operator interface 16 may be a patient bedside monitor or may also be a remote monitoring station in a dedicated room in a hospital or even in a remote location in telemedicine applications. Prior to being able to display vital sign information, the detected images need to be processed. The detected images may, however, comprise noise components. The main sources of noise are motion of the patient 10 and (ambient) light fluctuations. Hence, an appropriate signal processing is required. Usually, a plurality of time signals being more or less representative of vital signs (heart rate, breathing rate, blood oxygen saturation) is acquired. The acquisition may thereby be operated on a specific spectral range (visible, infrared, combination of selected spectral bands), maybe operated at global or local level (one time signal per skin measurement area versus several signals originating from the skin measurement area) and may involve techniques like principal component analysis, independent component analysis, local density approximation, linear projection into color subspaces, or signal decomposition techniques like wavelets, sinusoidal modeling and Empirical Mode Decomposition (EMD).

Figure 2:
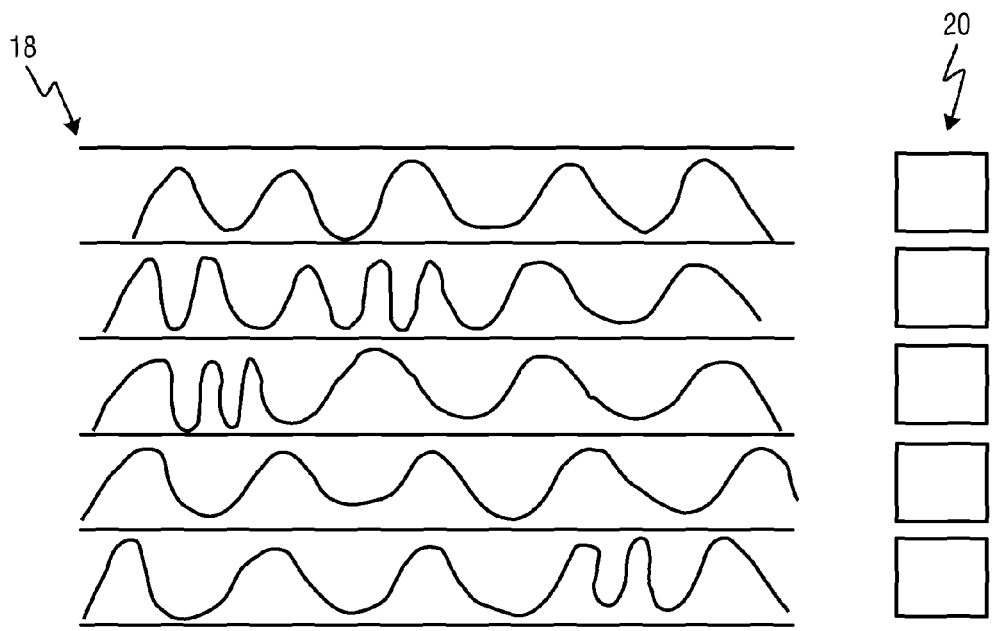
FIG. 2 shows a schematic illustration of a data stream comprising a plurality of input signals.

A data stream obtained from a camera 14 usually comprises a plurality of signals 18 as schematically illustrated in FIG. 2. These signals 18 may, e.g., represent the light intensities registered by the different pixels of a photo sensor (or also different colors). In order to determine a photoplethysmographic waveform the signals 18 are usually combined. One possibility for combining the signals is to calculate an average. It may, however, also be useful to combine only a subset of signals 18 and disregard some of the signals 18, in particular signals that are considered to be distorted and do not carry information on a vital sign of the patient. For this, the different signals 18 need to be processed (i.e. evaluated) in order to select "good" signals that are to be combined into the output signal. One way to process the signals 18 includes determining parameters 20 for the signals indicating whether or not the signal includes information on a vital sign of the patient 10 (signal information content parameters). Although it is possible to determine multiple parameters per signal or also one parameter for multiple signals, there is usually determined one parameter 20 for each of the signals. This parameter may thereby be a binary parameter or also a parameter on a predefined scale, i.e. a quality scale. Thereby a binary parameter allows directly indicating whether or not to include the signal into the output signal. A parameter on a quality scale may also allow determining the weight to attribute the signal when calculating the output signal. It is one goal of a device according to the present invention to process such signals (i.e. input signals).

Figure 3:
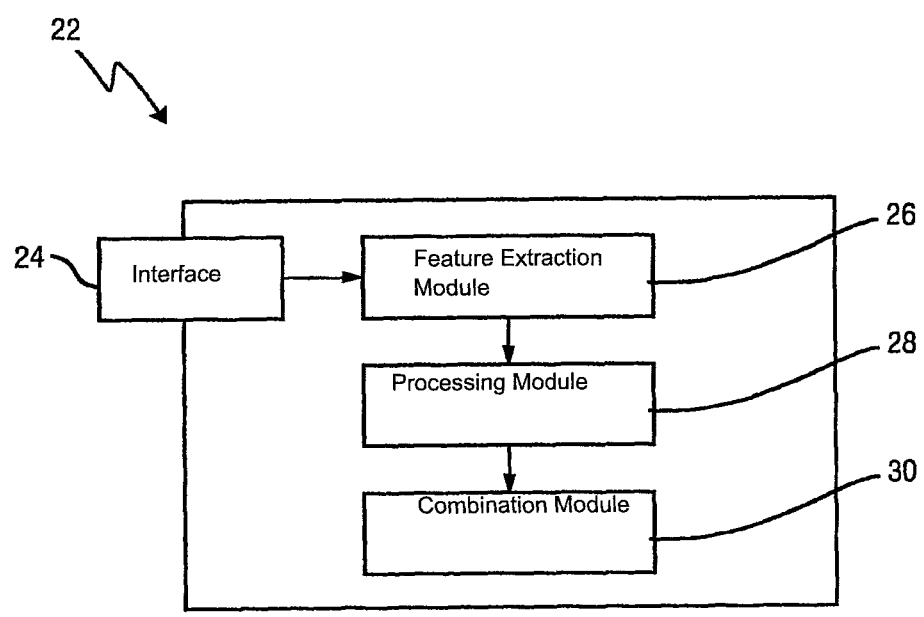
FIG. 3 shows an embodiment device for processing input signals related to a vital sign of a patient according to an aspect of the present invention.

FIG. 3 illustrates an embodiment of a device 22 according to the present invention. The device usually comprises an interface 24 at which a plurality of signals (i.e. input signals as, e.g., shown in FIG. 2) is received. This interface may, e.g., be connected to any kind of sensor, in particular a photo sensor or a camera. This sensor provides a data stream, in which there are included a plurality of input signals.

The main objective of the device 22 is to evaluate whether the input signals include meaningful information on a vital sign of the subject or whether the noise component in individual input signals is too high due to distortions. In order to determine said information, a feature extraction module 26 for extracting at least one feature of the input signal is provided. In particular, the instantaneous frequency representation and/or the instantaneous amplitude representation of an input signal is extracted. Other extracted features may also include a spectral representation of an input signal. The device 22 further includes a processing module 28 for determining at least one signal information content parameter for an input signal, i.e. one parameter for each of the input signals, based on the extracted features.

Optionally, the device 22 also includes a combination module 30 in which different input signals can be combined in order to determine a combined output signal characterizing the vital sign of the subject. Said combined output signal may particularly refer to a photoplethysmographic waveform. Returning to FIG. 1, this photoplethysmographic waveform can then be further processed in an evaluation unit 32 that may, e.g., be comprised in an operator interface 16 and that allows determining vital signs from the photoplethysmographic waveform.

A device according to an embodiment of the present invention may, e.g. be used to process input signals related to the heart rate of a patient. The input signals may, e.g. be obtained non-invasively by means of a camera sensor directed at a patient. There may be acquired a time signal including at least two consecutive frames. For instance a signal is acquired including 40 frames with a sampling rate of 20 frames per second (two seconds). It is to be determined, whether the input signals include information on the heart rate (i.e. the heart rate may be extracted from the signals in a further processing step). This heart rate usually exhibits the following properties:

1. It is quasi-periodic with limits on the range of its periodicity (range about 42 to 110 beats per minute).

2. It is quasi-stationary, i.e., its instantaneous frequency should only change within limits.

3. It is quasi-stationary, i.e., its instantaneous amplitude should only change within limits.

Figure 4A:
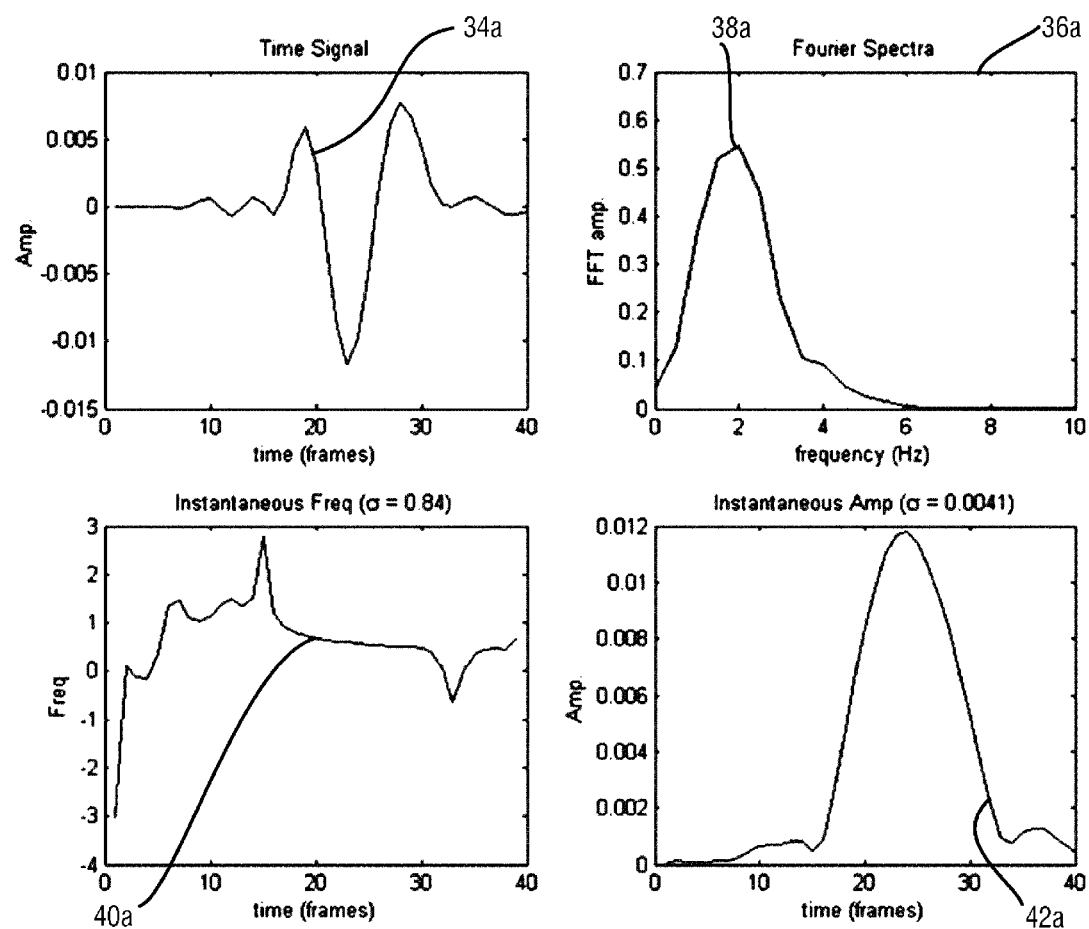
FIGS. 4*a* and 4*b* each show an illustration of extracted features from two different input signals.
Figure 4B:
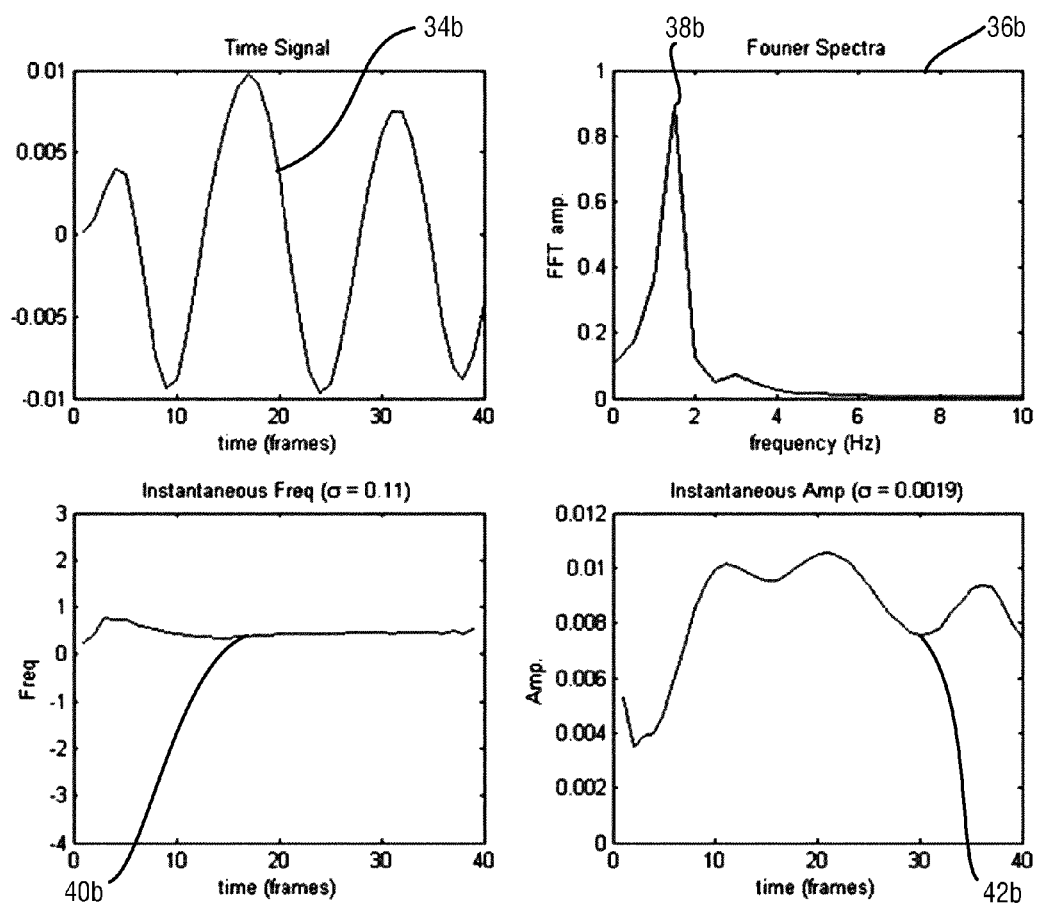

FIG. 4 illustrates examples for input signals and therefrom extracted features. In FIG. 4a, input signal 34a corresponds to a distorted signal, wherein the distortion may, e.g., be caused by a fluctuating light. Input signal 34b in FIG. 4b, in contrast thereto, represents a valid signal, i.e. a signal including information on the heart rate of the monitored patient.

For both input signals, a spectral representation is illustrated 36a, 36b. This spectral representation is usually extracted by means of a Fourier transform. Based on this spectral representation 36a, 36b, the dominant frequency 38a, 38b representing a signal information content parameter can be determined. It can be seen that, although input signal 34a does not represent a valid and meaningful signal, it still exhibits a strong frequency component in the relevant frequency interval, i.e. the dominant frequency or the peak 38a in the spectral representation is within a range that could be expected for the heart rate of a patient. The peaks 38a and 38b are more or less equivalent. Thus, relying on a dominant frequency criterion alone, would (for this example) not allow distinguishing between the valid signal 34b and the distorted (or invalid) signal 34a.

If, however, the instantaneous frequency representation 40a, 40b of the input signals 34a, 34b is also considered, it becomes possible to distinguish the two input signals.

The instantaneous frequency representation 40a may be extracted by using the Hilbert transform (alternative approaches therefor may, e.g., include evaluating the mean distance between consecutive zero crossings in the input signal or the standard deviation of distances between consecutive zero crossings as parameters indicative of aspects of the instantaneous frequency). It can be seen that the instantaneous frequency representation 40a of the distorted signal 34a is less stable over time than the instantaneous frequency representation 40b of the valid signal 34b. One possibility to make this accessible is to determine the standard deviation of the instantaneous frequency representation (representing a signal information content parameter). For the distorted input signal 34a and its instantaneous frequency representation 40a the standard deviation is 0.84. For the valid input signal 34b and its instantaneous frequency representation, the standard deviation is 0.11. Thus, a binary signal information content parameter could be determined by comparing the standard deviation to a predefined threshold (frequency threshold), e.g. a threshold of 0.2.

Additionally or alternatively to the instantaneous frequency representation of the input signal, the instantaneous amplitude representation 42a, 42b (sometimes also referred to as signal envelope) may be considered. This instantaneous amplitude representation 42a, 42b may also be extracted by using the Hilbert transform. It can be seen that the instantaneous amplitude representation 42a, i.e. the signal envelope of the (distorted) input signal 34a, is again less stable over time than the instantaneous amplitude representation 42b of the input signal 34b. One possible classification could thus again be based on a threshold on the standard deviation, i.e. an amplitude variation threshold. In the present example, the standard deviation of the instantaneous amplitude representation 42a is 0.0041, whereas the standard deviation of the instantaneous amplitude representation 42b is 0.0019. Therefore, a reasonable threshold, i.e. amplitude variation threshold, could be 0.0025. Again, a binary signal information content parameter may indicate whether this criterion is fulfilled.

For both, the instantaneous frequency representation as well as the instantaneous amplitude representation (extracted features), there may also be other metrics characterizing the variation over time (signal information content parameters) used for the distinguishing between valid and distorted signals. For example, the dynamic range could be used. The thresholds may also be adapted continuously (e.g. in form of a moving average). Alternatively to making use of the spectral representation of the signal, determining the dominant frequency may also include calculating the mean of the instantaneous frequency. In the illustrated example, the determined binary decision value represents one form of a signal information content parameter.

Figure 5:
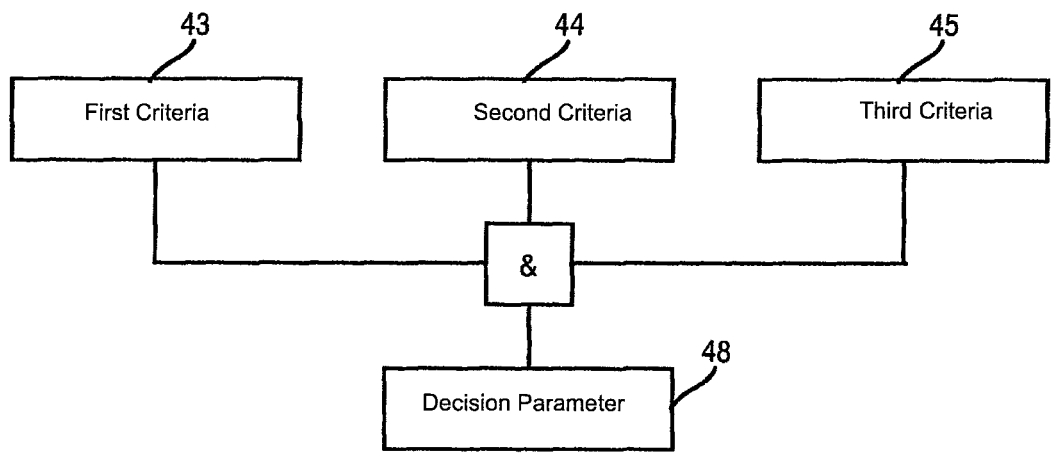
FIG. 5 schematically illustrates a possible approach to determine an output signal.

For distinguishing the input signals illustrated in FIG. 4, applying either a frequency or an amplitude variation threshold would thus suffice. In other embodiments of the present invention, determining which of a plurality of input signals to include when determining an output signal, i.e. a photoplethysmographic waveform, may also include combining multiple criteria. In FIG. 5, there is outlined one example therefor. A binary signal information content parameter is determined for an input signal based on a combination of three signal information content parameters (i.e. three criteria applied to three signal information content parameters). If all three criteria are fulfilled, the input signal is determined to be valid and to be included in the output signal, i.e. the binary signal information content parameter 48 is set to be 1. The first criterion 43 in the illustrated example is a range criterion, wherein it is determined that the dominant frequency component of the input signal lies within a frequency range. For the heart rate, a reasonable filtering range may be 0.5 to 3.5 Hz. The second criterion 44 is fulfilled if the standard deviation of the instantaneous frequency representation of the input signal is below a frequency variation threshold (e.g. 0.2 for the heart rate). The third criterion 45 is fulfilled if standard deviation of the instantaneous amplitude of the input signal is below an amplitude variation threshold (e.g. 0.0025 for the heart rate). If all criteria 43, 44, 45 are fulfilled, the decision parameter 48 is set to be valid.

An output signal may then be determined in a combination module by calculating the average of all input signals that fulfill the three criteria 43, 44, 45. It may thereby be possible to either calculate an average based on equally weighting all input signals to include or by individually weighting the input parameters, e.g. based on the inverse of the determined standard deviation of the instantaneous frequency amplitude representation of the signal, such that signals with a lower standard deviation are attributed a higher weight.

In other embodiments of the present invention, it may, however, also be possible that multiple signal information content parameters are determined from a single feature or that one single information content parameter is determined based on multiple features.

Obviously, other signal information content parameters and other thresholds are to be used if other vital signs are to be determined. Further, the present invention may also be adapted to work for continuously acquired signals or for different time samples.

Figure 6:
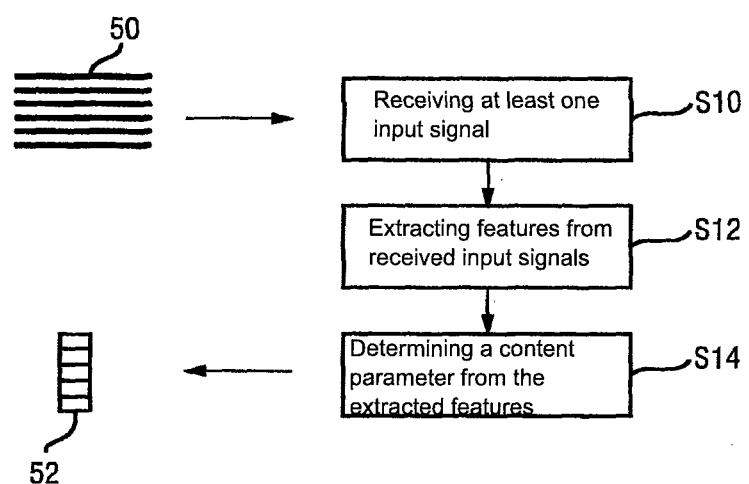
FIG. 6 schematically illustrates a method according to an aspect of the present invention.

In FIG. 6, a method for processing input signals is illustrated. This method comprises receiving at least one input signal 50 in step S10. This input signal 50 may particularly correspond to a non-invasively detected input signal, e.g. a signal derived from electromagnetic radiation reflected from region of interest including a skin area of a patient. In step S12 there are extracted features of that input signal. In particular, a Hilbert transform is performed and an analytic representation of the input signal is determined. An analytic representation of a signal usually includes two functions, usually referred to as the amplitude envelope and the instantaneous phase of the signal. The amplitude envelope of the input signal corresponds to the amplitude representation of the input signal, the time derivative of the unwrapped instantaneous phase is usually referred to as the instantaneous frequency or the instantaneous frequency representation of the input signal. In the last step S14, there is determined a signal information content parameter for the input signal or for each of a plurality of input signals 50, respectively. This signal information content parameter indicates whether the input signal includes information on a vital sign of the subject. The parameter or the plurality of parameters (usually one or more parameters per signal) 52 are provided for further processing. One particular application of the signal information content parameters 52 is their use in a combination module for combining the different input signals into one output signal. Combining the signals 50 may thereby particularly be based on averaging or weighted averaging the different input signals.

In a preferable embodiment of the present invention, the instantaneous frequency and instantaneous amplitude representations of the signal are based on determining an analytic representation of the signal by means of a Hilbert transform. This may particularly include the following steps (given a discrete-time signal x(n)):

i) Option 1:
determine by the Hilbert transformation the associated discrete-time signal y(n) of the discrete-time signal x(n) and from that create the analytic signal c(n)=x(n)+iy(n) with i the imaginary unit i=$\sqrt{(-1)}$ and n the sample index;
determine the instantaneous envelope e(n) and instantaneous phase p(n) from c by defining c(n)=e(n) exp(i p(n)) with e(n) a nonnegative real-valued discrete-time function and p(n) a real-valued discrete-time function with exp(.) denoting the exponential function;
determine the unwrapped phase u(n) from p(n) by taking u(n)=unwrap(p(n)) (unwrap is a Matlab function generally known by the skilled person);
determine the instantaneous frequency f(n) by a suitable difference operator, e.g. by a first-order forward difference according to f(n)=u(n+1)−u(n).

ii) Option 2:
determine by the Hilbert transformation the associated discrete-time signal y(n) of the discrete-time signal x(n) and from that create the analytic signal c(n)=x(n)+iy(n) with i the imaginary unit i=$\sqrt{(-1)}$ and n the sample index;
determine the instantaneous envelope e(n) and instantaneous phase p(n) from c(n) by taking e(n) equal to the absolute value of the complex number c(n), i.e., e(n)=$\sqrt{(x^2(n)+y^2(n))}$, and setting p(n) equal to the phase of the complex number c(n);
determine the unwrapped phase u(n) from p(n) by taking u(n)=unwrap(p(n));
determine the instantaneous frequency f(n) by a suitable difference operator, e.g. by a first-order forward difference according to f(n)=u(n+1)−u(n).

One main application of the present invention is in the determination of the heart rate of a patient being monitored by means of a camera. In further embodiments of the present invention, it may, however, also be possible to apply the outlined principles to conventional PPG measurements using an LED and a photodiode as e.g. used in a fingerclip-type sensor. Therein, the input signal obtained by means of a reflectivity or transmissivity measurement is evaluated based on its instantaneous phase and amplitude in addition to the evaluation of its dominant frequency. Analogously to the above outlined selection scheme, the input signal is only further processed, if the three features (or a subset thereof) fulfill predefined or adaptively defined threshold criteria.

By way of example, the present invention can be applied in the field of health care, e.g. unobtrusive remote patient monitoring, general surveillances, security monitoring and so-called lifestyle environments, such as fitness equipment, or the like. Applications may include monitoring of oxygen saturation (pulse oximetry), heart rate, blood pressure, cardiac output, changes of blood perfusion, assessment of autonomic functions, and detection of peripheral vascular diseases. It may also be possible to determine these or other vital signs based on other criteria applied to the instantaneous frequency and amplitude representation and dominant frequency of the signal.

Needless to say, in an embodiment of the method in accordance with the invention, several of the steps described herein can be carried out in changed order, or even concurrently. Further, some of the steps could be skipped as well without departing from the scope of the invention.

The different modules comprised in a device according to the present invention may be implemented in software on one or multiple processors. Alternatively, some or all modules may also be (partly or completely) implemented in hardware.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device configured to process input signals related to a vital sign of a subject, the device comprising:
a camera configured to convert light reflected from a region of interest into a data stream and to extract a plurality of input signals from said data stream, the camera comprising a CCD or CMOS sensor;
an interface configured to receive a plurality of non-invasively detected input signals from the camera;
a feature extraction module configured to extract at least one feature of each input signal of the plurality of input signals, said at least one feature including at least an instantaneous frequency representation of the input signal;
a processing module configured to determine a signal information content parameter for each input signal of the plurality of input signals based on the at least one extracted feature, said signal information content parameter being indicative of information on a vital sign of the subject included in the input signal; and
a combination module configured to:
combine the plurality of input signals based on the signal information content parameters of the plurality of input signals into a combined output signal characterizing the vital sign of the subject; and
determine an average of the plurality of input signals, based on attributing individual weights to the plurality of input signals, said individual weights being calculated based on the signal information content parameters of the plurality of input signals;
an evaluation unit configured to determine vital sign information of the subject based on the determined average plurality of input signals; and
a display device configured to display the determined vital sign information.

2. The device as claimed in claim 1, wherein the at least one feature further includes an instantaneous amplitude representation of the input signal, and wherein the feature extraction module is configured to:
determine an analytic representation of the input signal by applying a Hilbert transform to the input signal; and
determine the absolute value of the analytic representation of the input signal for extracting the instantaneous amplitude representation of the input signal.

3. The device as claimed in claim 1, wherein the at least one extracted feature further includes a spectral representation of the input signal.

4. The device as claimed in claim 1, wherein the feature extraction module is configured, for extracting the instantaneous frequency representation of the input signal, to at least one of:
determine an analytic representation of the input signal by applying a Hilbert transform to the input signal, to extract from the analytic representation of the input signal an instantaneous phase representation of the input signal and to determine the derivative of the instantaneous phase representation of the input signal; and
determine the mean and/or variance of distances between consecutive zero crossings of the input signal as parameters indicative of the instantaneous frequency representation of the input signal.

5. The device as claimed in claim 1, wherein the processing module is configured to determine a dominant frequency component of the input signal by calculating an average of the instantaneous frequency representation of the input signal.

6. The device as claimed in claim 1, wherein the at least one feature further includes an instantaneous amplitude representation of the input signal, and wherein the processing module is configured to at least one of:
determine a standard deviation of the instantaneous frequency representation of the input signal; and
determine a standard deviation of the instantaneous amplitude representation of the input signal.

7. The device as claimed in claim 6, wherein the processing module is further configured to at least one of:
compare the standard deviation of the instantaneous frequency representation of the input signal with a frequency variation threshold; and compare the standard deviation of the instantaneous amplitude representation of the input signal with an amplitude variation threshold.

8. The device as claimed in claim 1, wherein the processing module is configured to:
determine a dominant frequency component of the input signal by determining the frequency with the highest spectral intensity in a spectral representation of the input signal or by calculating an average of the instantaneous frequency representation of the input signal; and
determine whether the dominant frequency component of the input signal is within a frequency range.

9. The device as claimed in claim 1, wherein the processing module is configured to determine a binary signal information content parameter for the input signal based on a conjunction of at least two threshold or range criteria applied to the signal information content parameter, said binary signal information content parameter indicating whether the input signal includes information on a vital sign of the subject.

10. The device as claimed in claim 1, wherein the input signal is derived from electromagnetic radiation reflected from a region of interest including a skin area of the subject and the vital sign of the subject corresponds to the heart rate, respiration rate or blood oxygen saturation of a living subject.

11. The device as claimed in claim 1, wherein the combination module is configured to determine whether to use or discard an input signal for the combination of input signals based on the respective signal information content parameters and to combine only non-discarded input signals.

12. A monitoring system configured to remotely monitor a vital sign of a subject comprising
a sensor configured to convert light reflected from a region of interest into a data stream and to extract a plurality of input signals from said data stream;
a device as claimed in claim 1.

13. A non-transitory computer readable medium storing instructions executable by a processor to perform a method for processing input signals related to a vital sign of a subject, the method comprising
with a camera, converting light reflected from a region of interest into a data stream and to extract a plurality of input signals from said data stream, the camera comprising a CCD or CMOS sensor;
with the processor:
receiving a plurality of non-invasively detected input signals from the camera;
extracting at least one feature of each input signal of the plurality of input signals, said at least one feature including an instantaneous frequency representation of the input signal;
determining a signal information content parameter for each input signal of the plurality of input signals based on the at least one extracted feature, said signal information content parameter being indicative of information on a vital sign of the subject included in the input signal; and
combining the plurality of input signals based on the signal information content parameters of the plurality of input signals into a combined output signal characterizing the vital sign of the subject, wherein the step of combining includes determining an average of the plurality of input signals, based on attributing individual weights to the plurality of input signals, said individual weights being calculated based on the signal information content parameters of the plurality of input signals;
determining vital sign information of the subject based on the determined average plurality of input signals; and
displaying, on a display device, the determined vital sign information.

14. The non-transitory computer readable medium as claimed in claim 13, wherein the at least one feature further includes an instantaneous amplitude representation of the input signal, and wherein extracting at least one feature of each input signal of the plurality of input signals, said at least one feature including an instantaneous frequency representation of the input signal and/or an instantaneous amplitude representation of the input signal further includes at least one of:
determining an analytic representation of the input signal by applying a Hilbert transform to the input signal, to extract from the analytic representation of the input signal an instantaneous phase representation of the input signal and to determine the derivative of the instantaneous phase representation of the input signal; and
determining the mean and/or variance of distances between consecutive zero crossings of the input signal as parameters indicative of the instantaneous frequency representation of the input signal.

15. The non-transitory computer readable medium as claimed in claim 13, further including:
deriving the input signal from electromagnetic radiation reflected from a region of interest including a skin area of the subject and the vital sign of the subject corresponds to the heart rate, respiration rate or blood oxygen saturation of a living subject.

16. The non-transitory computer readable medium as claimed in claim 13, further including:
determining whether to use or discard an input signal for the combination of input signals based on the respective signal information content parameters and to combine only non-discarded input signals.

17. A monitoring apparatus configured to remotely monitor a vital sign of a subject, the apparatus comprising:
a camera configured to convert light reflected from a region of interest into a data stream and to extract a plurality of input signals from said data stream, the camera comprising a CCD or CMOS sensor;
an interface configured to receive the plurality of input signals extracted from the data stream; and
at least one processor programmed to:
extract at least one feature of each input signal of the plurality of input signals, said at least one feature including an instantaneous frequency representation of the input signal;
determine a signal information content parameter for each input signal of the plurality of input signals based on the at least one extracted feature, said signal information content parameter being indicative of information on a vital sign of the subject included in the input signal;
combine the plurality of input signals based on the signal information content parameters of the plurality of input signals into a combined output signal characterizing the vital sign of the subject;
determine an average of the plurality of input signals, based on attributing individual weights to the plurality of input signals, said individual weights being calculated based on the signal information content parameters of the plurality of input signals; and determine vital sign information of the subject based on the determined average of the plurality of input signals; and a display device configured to display the determined vital sign information.

18. The apparatus as claimed in claim 17, wherein the at least one processor is further programmed to extract the instantaneous frequency representation of the input signal by at least one of:

determining an analytic representation of the input signal by applying a Hilbert transform to the input signal, to extract from the analytic representation of the input signal an instantaneous phase representation of the input signal and to determine the derivative of the instantaneous phase representation of the input signal; and determining the mean and/or variance of distances between consecutive zero crossings of the input signal as parameters indicative of the instantaneous frequency representation of the input signal.

19. The apparatus as claimed in claim 17, wherein the at least one processor is further programmed to:

derive the input signals from electromagnetic radiation reflected from a region of interest including a skin area of the subject and the vital sign of the subject corresponds to the heart rate, respiration rate or blood oxygen saturation of a living subject.

20. The apparatus as claimed in claim 17, wherein the at least one processor is further programmed to determine whether to use or discard an input signal for the combination of input signals based on the respective signal information content parameters and to combine only non-discarded input signals.

* * * * *